United States Patent [19]
Metters

[11] Patent Number: 4,830,183
[45] Date of Patent: May 16, 1989

[54] DISPENSER APPARATUS

[75] Inventor: John R. Metters, Hingham, Mass.

[73] Assignee: Aegis Medical Corporation, Weymouth, Mass.

[21] Appl. No.: 136,695

[22] Filed: Dec. 22, 1987

[51] Int. Cl.⁴ .............................................. A61B 17/06
[52] U.S. Cl. ...................................... 206/441; 221/70; 156/584
[58] Field of Search ....................... 221/71, 72, 73, 70; 156/584, DIG. 33; 128/155, 169, 170; 206/441, 390

[56] References Cited

U.S. PATENT DOCUMENTS

| | | | |
|---|---|---|---|
| 3,107,193 | 10/1963 | DeNeui et al. | 156/584 X |
| 3,107,814 | 10/1963 | Auger et al. | 221/73 |
| 3,698,600 | 10/1972 | Foote | 221/73 X |
| 3,839,127 | 10/1974 | Hazuka | 156/584 X |
| 4,525,237 | 6/1985 | Clar | 156/DIG. 33 X |
| 4,626,313 | 12/1986 | Karp | 156/DIG. 33 X |

Primary Examiner—Joseph J. Rolla
Assistant Examiner—Gregory L. Huson
Attorney, Agent, or Firm—Lahive & Cockfield

[57] ABSTRACT

An apparatus useful for storing and dispensing articles which are releasably secured to a continuous length of release paper. The apparatus includes a dispensing guide adapted to receive the strip of release paper. The dispensing guide includes a passageway which deforms the release paper as it passes therethrough thus enabling the adhered articles to be easily peeled from the release strip. Also provided is a method for removing articles removeably adhered to a strip of release paper.

14 Claims, 4 Drawing Sheets

DISPENSER APPARATUS

BACKGROUND OF THE INVENTION

The present invention is directed to a dispenser for articles adhered to a strip of release paper.

Articles which are adhesively backed are normally adhered to a strip of release paper for convenient storage prior to use. Typically, a multitude of such articles are adhered to a relatively long strip of release paper. Removal of these articles from the release paper can sometimes be difficult as the strip must be manipulated and sometimes contorted in order to peel a useful article from the strip. This process can result in damage to the useful articles and also can be relatively time consuming and inconvenient, especially when one has an immediate use for an article. Accordingly, it would be advantageous to provide a dispenser to facilitate rapid and convenient removal of useful articles adhered to a strip of release paper.

SUMMARY OF THE INVENTION

Accordingly, it is an object of the present invention to provide a dispenser to facilitate rapid and convenient removal of articles adhered to a strip of release paper. Another object of the invention is to provide an apparatus to facilitate the convenient and rapid removal of medical dressing barriers from a strip of release paper. A further object of the invention is to provide a method of conveniently dispensing such articles. Other objects of this invention will be apparent to those of ordinary skill in the art upon reading this disclosure.

The present invention thus provides an apparatus for storing and dispensing articles which are removably adhered to a strip of release paper. The apparatus comprises a box or other container having a lid with a slot disposed therein. A dispensing guide, having a passageway disposed between an inlet portion and an outlet portion of the guide, is mounted to the lid adjacent the slot. The passageway of the dispensing guide also has disposed therein an elevated, generally triangular-shaped ridge which forms a bottom portion of the passageway. The elevated ridge gradually increases in height and width between the inlet and the outlet of the guide.

The present invention is used by directing a strip of release paper having useful articles removably adhered thereto through the slot in the lid and then into the passageway of the dispensing guide. As the release paper is drawn through the guide, the increasing height of the ridge causes the paper to deform. As a result, the useful articles may not deform to the extent of the release paper and may be easily peeled from the release paper. In a preferred embodiment, the useful article features a tab means for facilitating gripping of the article. As the strip and the adhered articles pass through the guide, the deformation of the strip and articles causes the tab to protrude from the article and thus become easy to grasp.

BRIEF DESCRIPTION OF THE DRAWINGS

For greater understanding of the nature and objects of the invention, reference should be made to the following detailed description and the accompanying drawings in which.

DETAILED DESCRIPTION OF THE INVENTION

Figure 1:
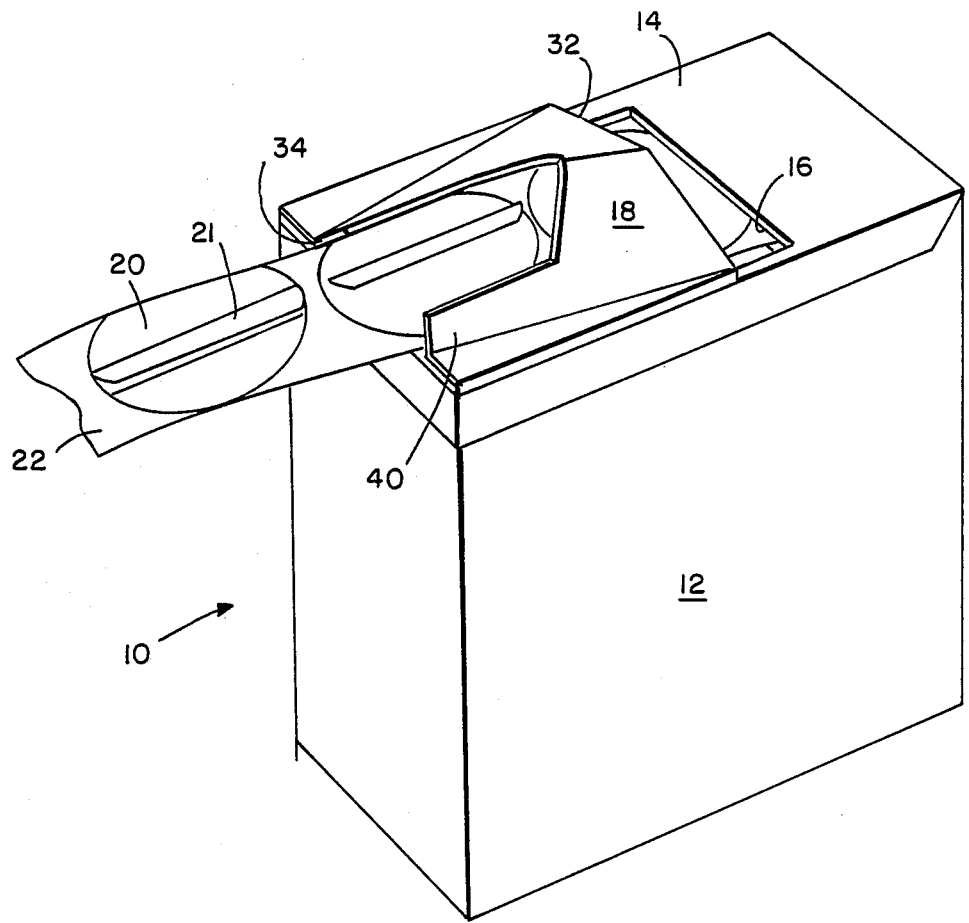
FIG. 1 is a perspective view of the dispenser apparatus of the present invention, illustrating a dispensing guide through which a release strip bearing useful articles is passed.
Figure 2A:
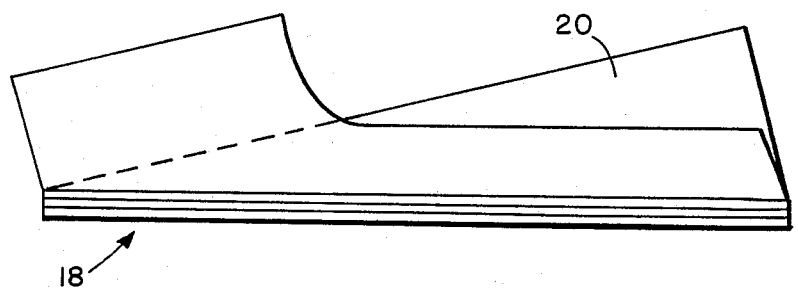
FIG. 2A is a side view of the dispensing guide of FIG. 1.
Figure 2B:
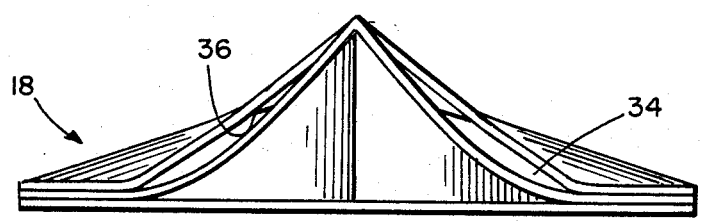
FIG. 2B is a front view of the dispensing guide of the apparatus of FIG. 1.
Figure 2C:
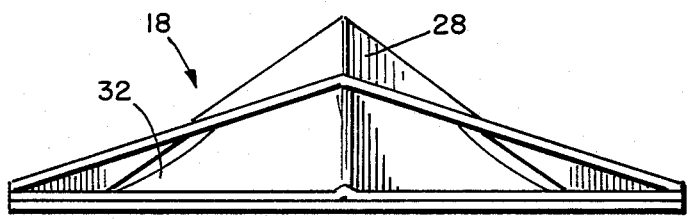
FIG. 2C is a rear view of the dispensing guide of the apparatus of FIG. 1.
Figure 2D:
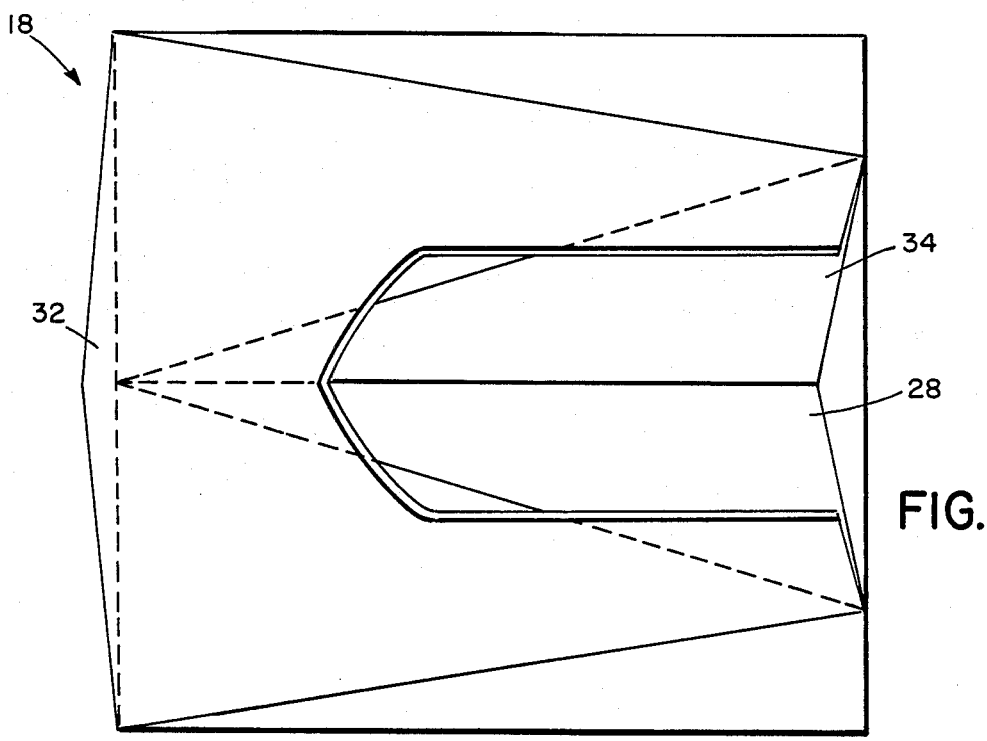
FIG. 2D is a top view of the dispensing guide of the apparatus of FIG. 1.
Figure 3:
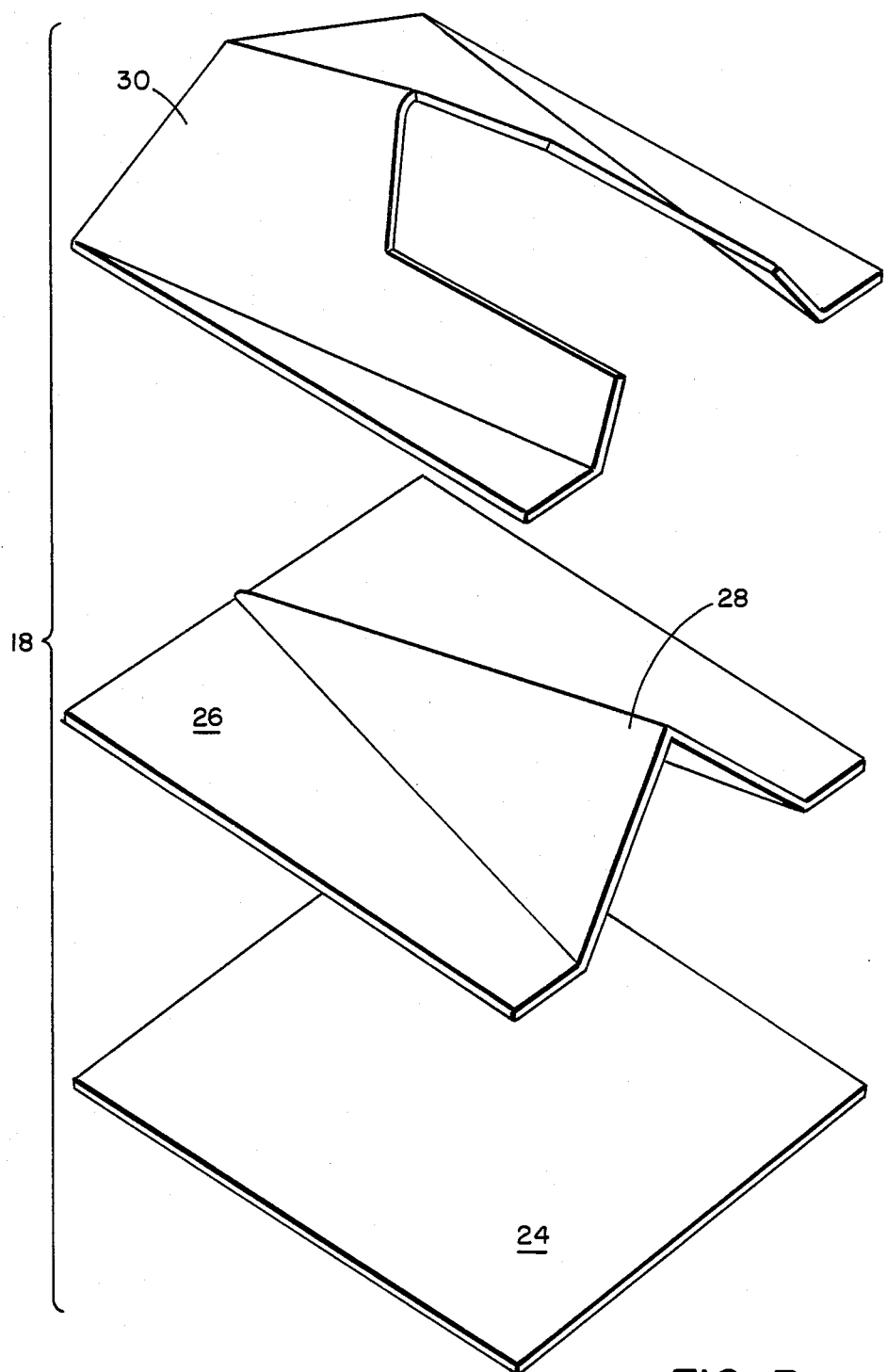
FIG. 3 is an exploded view of the dispensing guide of the apparatus of FIG. 1.
Figure 4:
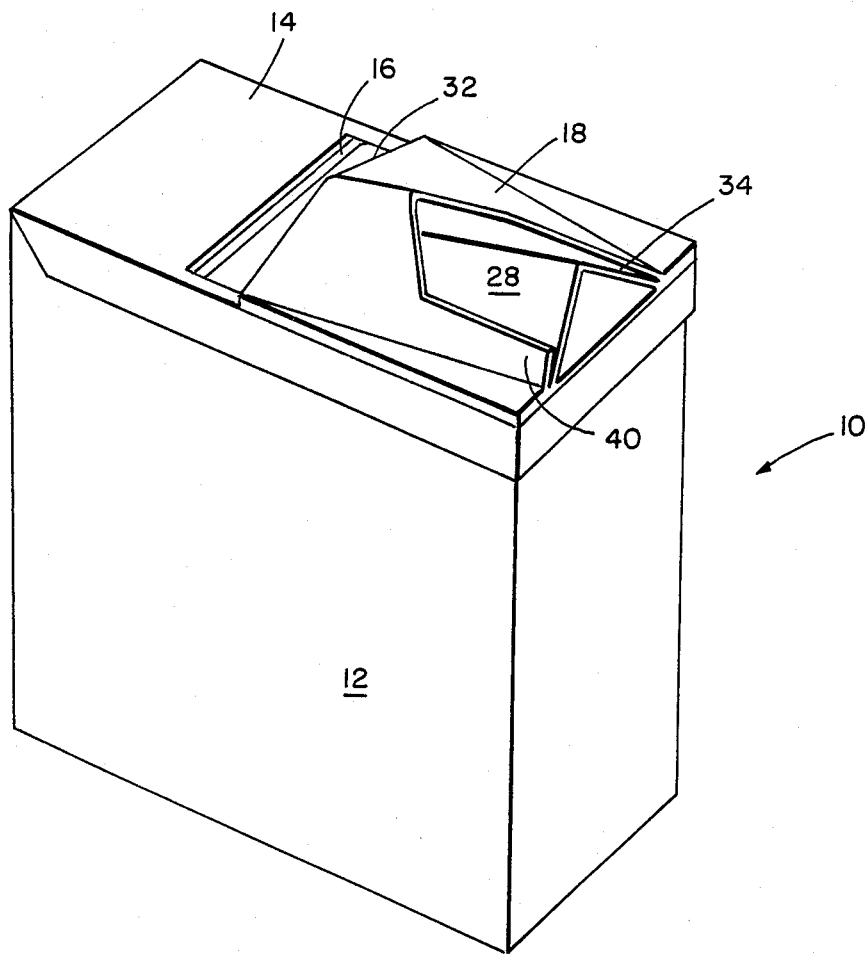
FIG. 4 is a perspective view of the apparatus of FIG. 1.

Referring to FIGS. 1 and 4 a dispensing apparatus 10 includes a box means 12 having a lid 14 which features a slot 16 disposed in its top surface. Dispensing apparatus 10 also includes a dispensing guide 18 which may be permanently affixed to the top portion of the lid adjacent the slot, or removably and replaceably secured to the top surface of the lid. As shown in FIG. 1, dispensing apparatus 10 may be used to facilitate storage and dispensing of medical dressing barrier devices 20 which are secured to a continuous length of release paper 22. The medical dressing barriers which may be used in conjunction with the present invention are those disclosed in U.S. patent application Ser. No. 93,502, filed Sept. 4, 1987, which is hereby incorporated by reference.

The dispensing apparatus 10 may be used to dispense not only medical dressing barriers 20, but virtually any other useful article which is adhesively secured to a strip of release paper. Accordingly, the dimensions of dispensing apparatus 10 and its various components are not critical, but depend upon the requirements of a particular application. Such dimensions would of course be obvious to one of ordinary skill in the art.

FIGS. 1, 2A–2D and FIG. 3 illustrate the dispensing guide 18 of dispensing apparatus 10. As shown best in FIG. 3, dispensing guide 18 comprises a bottom surface 24 intermediate layer 26 having a raised ridge portion 28 and a top surface 30. Dispensing guide 18 also features an inlet portion 32 at its rear end and an outlet portion 34 at its front end.

The top sheet 30 of guide apparatus 18 comprises a raised portion 38 proximal to the inlet (rear) end of the guide. Angularly oriented arms 40, which diverge inwardly, extend forwardly from raised portion 38 toward the outlet end of the guide. Arms 40 are separated by an opening within the central portion of sheet 30. This opening is adapted to receive raised ridge 28 which protrudes from a bottom portion of guide 18.

Dispensing guide 18 is constructed such that inlet 32, disposed at the rear end of the guide, is relatively wide and has ample vertical clearance to enable a strip of paper 22 to be inserted through the inlet 32 and held loosely within inlet 32. Raised ridge 28 extends from the bottom portion of dispensing guide 18 and gradually increases in height and width in a direction from the inlet end to the outlet end of the guide. The increasing height of ridge 28 lessens the gap in the passageway 36 which is disposed between inlet 32 and outlet 34 of guide 18 thus reducing the vertical clearance within the passageway.

Passageway 36 also decreases in width as the outlet end 34 is approached. Thus outlet 34 is relatively narrow, preferably being narrower in width than release paper 22. In addition, the passageway 36 at the outlet 34, which is defined by the bottom surfaces of arms 40 and the top surface of raised ridge 28, provides little vertical clearance for release paper 22 and any attached articles.

Dispensing apparatus 10 is preferably used as a packaging unit for useful articles which are releasably adhered to a continuous strip of release paper. The release paper may be packaged within box 12 in roll form, or another suitable form, and the package may be sealed by closing the lid. To utilize the dispenser a leading edge of strip 22 may be guided through slot 16 and into the inlet opening 32 of dispensing guide 18. The release strip is then threaded through the passageway 36 of dispenser guide 18 and the leading edge is allowed to extend slightly beyond the outlet 34 of guide 18. As noted above, the inlet opening 32 is relatively wide and has a substantial amount of vertical clearance in order to loosely engage strip 22. However, the passageway gradually decreases in width and vertical clearance in the direction of the outlet opening 34. At outlet opening 34 itself, the strip is securely held between angular arms 40 and raised ridge 28 such that a strip of release paper passing through passageway 36 is deformed upon its exit from outlet 34. By deforming the release paper any useful article borne by the release paper is also deformed to some extent and may then be easily removed from the release paper. In a preferred embodiment, however, the release paper carries an article, such as medical dressing barrier devices 20, which include a protruding tab 21. Normally, tab 21 is flush against the surface of barrier 20 and it is thus difficult to grasp 21 to facilitate the peeling of barrier 20 from strip 22. When barrier 20 bearing tab 21 passes through passageway 36 of guide 18. The release paper and barrier itself are deformed to the extent that they allow tab 21 to protrude slightly from the surface of barrier 20. In this way, tab 21 is easily grasped and used to remove the barrier from the release strip.

While the embodiment described has been shown with a rectangular container and a sharp-peaked triangular ridge, other geometrical configurations are also suitable. For example, the guide might have a cylindrical configuration with a generally rounded ridge. Similarly, the container could have a curved or circular lid portion.

Although the dispensing apparatus of the present invention has been described primarily with respect to the dispensing of medical dressing barriers, it is understood that other useful articles may be used with the dispensing apparatus of the present invention. Also, it is understood that the dispensing apparatus of the present invention is not to be limited by any particular dimension or construction material. The dimensions of such apparatus and the materials from which it is made will depend upon the applications which are desired and will be readily apparent to those of ordinary skill in the art.

Having described the invention, what is claimed is:

1. A dispenser apparatus, comprising:
   a container means for retaining a supply of release paper having adhered thereto a plurality of removable articles, said container means having a lid with a slot disposed therein;
   a guide disposed on said container means, exterior to and adjacent said slot, said guide having a passageway for said release paper disposed between an inlet end and an outlet end; and
   a ridge means for deforming said release paper and removable articles, said ridge means being disposed within said passageway and having an elevation which progressively increases in a direction from the inlet end of said guide to the outlet end of said guide.

2. Apparatus of claim 1 wherein said inlet and outlet ends of the guide are defined by a bottom surface of said guide and a top surface of said guide.

3. Apparatus of claim 2 wherein the top surface of the guide is non-continuous proximal to the outlet end of the guide.

4. Apparatus of claim 3 wherein the width of the inlet is greater than the width of the outlet.

5. Apparatus of claim 4 wherein the width of the outlet is less than the width of the release paper.

6. Apparatus of claim 1 wherein said removeable articles comprise medical dressing barrier devices.

7. Apparatus of claim 5 wherein said guide is mounted on said lid.

8. Apparatus of claim 7 wherein said guide is removably and replaceably mounted on said lid means.

9. Apparatus of claim 7 wherein said guide is permanently mounted on said lid means.

10. Apparatus of claim 7 wherein said passageway is adapted to receive and guide a section of release paper which extends from said inlet through said outlet.

11. A method of removing adhered articles from a length of release paper, comprising the steps of:
    providing a container means for retaining a supply of release paper having articles adhered thereto;
    providing a guide means having a passageway disposed between an inlet and an outlet, said passageway having a raised ridge means disposed therein for deforming said release paper and adhered articles, said ridge means having an elevation which increases from the inlet end to the outlet end; and
    directing a strip of release paper having articles removably adhered thereto from said container means, through said passageway such that as said supply of release paper is advanced through said passageway it deforms allowing said articles to be removed therefrom.

12. The method of claim 11 wherein said articles comprise medical dressing barrier devices.

13. The method of claim 12 wherein said medical dressing barrier devices include a tab means.

14. The method of claim 13 wherein said tab means is caused to protrude from the surface of said medical dressing barrier device as it exits the outlet of said guide means.

* * * * *